United States Patent [19]

Webber et al.

[11] Patent Number: 5,945,408
[45] Date of Patent: Aug. 31, 1999

[54] HYDROXYANIDINO DERIVATIVES USEFUL AS NITRIC OXIDE SYNTHASE INHIBITORS

[75] Inventors: R. Keith Webber, St. Peters; Foe S. Tjoeng, Manchester; Robert E. Manning, St. Louis, all of Mo.

[73] Assignee: G.D. Searle & Co., Chicago, Ill.

[21] Appl. No.: 08/689,463

[22] Filed: Aug. 8, 1996

Related U.S. Application Data

[60] Provisional application No. 60/012,904, Mar. 6, 1996.

[51] Int. Cl.⁶ .................. C07F 7/08; C07F 7/10; A01N 55/00
[52] U.S. Cl. .................. 514/63; 548/240; 548/245; 548/349.1; 540/485; 540/487; 540/528; 549/215; 549/451; 549/452; 556/418; 556/419; 556/420; 556/422; 562/26; 562/27; 562/433; 562/440; 560/147; 560/153; 560/156; 560/168; 564/225; 564/229
[58] Field of Search .................. 548/240, 245, 548/349.1; 540/485, 487, 528; 549/215, 451, 452; 556/419, 418, 420, 422; 562/26, 27, 433, 440, 899; 560/147, 153, 156, 168; 564/225, 229; 514/63, 211, 378, 386, 389, 398, 467, 561, 562, 529, 546, 551, 256

[56] References Cited

U.S. PATENT DOCUMENTS

| | | |
|---|---|---|
| 4,046,909 | 9/1977 | Rasmussen et al. . |
| 4,061,746 | 12/1977 | Blohm et al. . |
| 4,443,468 | 4/1984 | Maillard et al. . |
| 4,523,020 | 6/1985 | Moormann et al. . |
| 4,533,739 | 8/1985 | Pitzele et al. . |
| 4,579,951 | 4/1986 | Pitzele et al. . |
| 5,028,627 | 7/1991 | Kilbourn et al. . |
| 5,059,712 | 10/1991 | Griffith . |
| 5,081,148 | 1/1992 | Braquet et al. . |
| 5,132,453 | 7/1992 | Griffith . |
| 5,216,025 | 6/1993 | Gross et al. . |
| 5,246,971 | 9/1993 | Williamson et al. . |
| 5,266,594 | 11/1993 | Dawson et al. . |
| 5,273,875 | 12/1993 | Griffith . |
| 5,684,008 | 11/1997 | Hallinan et al. .......... 514/256 |

FOREIGN PATENT DOCUMENTS

| | | |
|---|---|---|
| 191584 | 10/1978 | Czech Rep. . |
| 0370320 | 5/1990 | European Pat. Off. . |
| 0446699 | 9/1991 | European Pat. Off. . |
| 0462948 | 12/1991 | European Pat. Off. . |
| 0676196 | 10/1995 | European Pat. Off. . |
| 0713704 | 5/1996 | European Pat. Off. . |
| 0713876 | 5/1996 | European Pat. Off. . |
| 0717040 | 6/1996 | European Pat. Off. . |
| 1367598 | 9/1974 | United Kingdom . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/12163 | 6/1994 | WIPO . |
| 94/12165 | 6/1994 | WIPO . |
| 94/14780 | 7/1994 | WIPO . |
| 94/16729 | 8/1994 | WIPO . |
| 95 00505 | 1/1995 | WIPO . |
| 95 24382 | 9/1995 | WIPO . |
| 95 25717 | 9/1995 | WIPO . |
| 95/31987 | 11/1995 | WIPO . |
| 95/32203 | 11/1995 | WIPO . |
| 96 15120 | 5/1996 | WIPO . |
| 96/14842 | 5/1996 | WIPO . |
| 96/14844 | 5/1996 | WIPO . |

OTHER PUBLICATIONS

Perrin et al., "Absence of Stereoelectronic Control in Hydrolysis of Cyclic Amidines", *J. Am. Chem. Soc.*, vol. 108, No. 19, pp. 5997–6003, 1986.

Huber et al., "Saturated Heterocycles, Part 88. Synthesis of a New Ring System: Dipyrido–[1.2–α:4,3–d] pyrimidin–11–one Derivatives", *J. Chem. Soc. Perkin Trans. 1*, pp. 909–912, 1987.

Kökösi et al., "Nitrogen Bridgehead Compounds. Part 19(1). Synthesis of Polymethylenepyrimidin–4–ones", *J. Heterocyclic Chem.*, vol. 19, pp. 909–912, 1982.

Brown et al., Hydropyrimidines, Part II, pp. 4041–4045, 1962.

Adcock et al., 2–Amino–2–imidazolines 2–Amino–2–oxazolines, Part II, pp. 474–479, 1965.

Stefanye et al., "Cyclic Guanidines from Nitrimino Compounds", *J. Am. Chem. Soc.*, vol. 77, No. 3, pp. 761–762, 1955.

Klayman et al., "2–Amino–2–thiazoline. VII. Unequivocal Structure Assignment of the Products of the Reaction of 2–Amino–2–thiazoline and Its Analogs with Carbethoxy Isothiocyanate", *J. Org. Chem.*, vol. 39, No. 13, pp. 1819–1823, 1974.

Moriconi et al., "Synthesis and Reactions of Cyclic Amidines", *J. Org. Chem.*, vol. 33, No. 5, pp. 2109–2111, 1968.

Wagenaar et al., "Methodology for the Preparation of N–Guanidino–Modified Arginines and Related Derivatives", *J. Org. Chem.*, vol. 58, No. 1, pp. 4331–4338, 1993.

Gutteridge, "Acylation of 2–Amino–5, 5–dimethyl–Δ–pyrroline 1–Oxide", *J. Chem. Soc.*, (C), pp. 3121–3125, 1971.

Langlois et al., "Derivatives and Imidazole, 1,3,4–triazole and tetrazole", *J. Heterocycl. Chem.*, vol. 19, No. 1, pp. 193–200, 1982 (English Summary, p. 200).

Langlois et al., "Synthesis and Antidepressant Properties of 2–Amino–4–phenyl–1–pyrroline Derivatives", *Eur. J. Med. Chem.*, vol. 13, No. 2, pp. 161–169, 1978 (English Summary, p. 169).

(List continued on next page.)

*Primary Examiner*—Paul F. Shaver
*Attorney, Agent, or Firm*—Alan L. Scrivner; Dennis A. Bennett

[57] ABSTRACT

The current invention discloses hydroxyamidino derivatives useful as nitric oxide synthase inhibitors.

10 Claims, No Drawings

OTHER PUBLICATIONS

Klötzer et al., "Acylderivatives of 2–Amino–1–pyrrolines", *Monatshefte für Chemie*, vol. 102, No. 2, pp. 627–634, 1971 (English Summary, p. 627).

Klötzer et al. "Synthesis of Substituted 2–Amino–1–pyrrolines, I." *Monatshefte für Chemie*, vol. 101, No. 5, pp. 1263–1270, 1970 (English Summary, p. 1263).

Nakane et al., "Novel Potent and Selective Inhibitors of Inducible Nitric Oxide Synthase", *Molecular Pharmacology*, vol. 47, pp. 831–834, 1995.

Dunbar et al., "Design, Synthesis, and Neurochemical Evaluation of 2–Amino–5–(alkoxycarbonyl)–3,4,5,6–tetrahydopyridines and 2–Amino–5–(alkoxycarbonyl)–1,4,5,6–tetrahydropyrimidines as $M_1$ Muscarinic Receptor Agonists", *J. Med. Chem.*, vol. 37, No. 17, pp. 2774–2782, 1994.

Klötzer et al. "Synthesis of Substituted 2–Aminopyrrolines, II." *Monatshefte für Chemie*, vol. 101, No. 6, pp. 1841–1850, 1970 (English Summary, p. 1841).

Berge et al., "Pharmaceutical Salts", *J. Pharm. Sci.*, vol. 66, No. 1, pp. 1–19, 1977.

Moncada et al., "Nitric Oxide: Physiology, Pathophysiology, and Pharmacology", *Pharmacological Reviews*, Vo. 43, No. 2, pp. 109–142, 1991.

Moncada et al., "Biosynthesis of Nitric Oxide from L–Arginine", *Biochemical Pharm.*, vol. 38, No. 11, pp. 1709–1715, 1989.

Mazurek et al., "Theoretical Studies of Tautomerism of Clonidine Vacuum and in Water Medium", *Theochem*, 82(1–2), 23–8, 1991.

HYDROXYANIDINO DERIVATIVES USEFUL AS NITRIC OXIDE SYNTHASE INHIBITORS

This application claims benefit of U.S. Provisional application No. 60/012904 filed Mar. 6, 1996.

BACKGROUND OF THE INVENTION

1. Field of the Invention

The present invention relates to hydroxyamidino derivatives and their use in therapy, in particular their use as nitric oxide synthase inhibitors.

2. Related Art

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, congestive heart failure, hyperalgesia (allodynia), cerebral ischemia (both focal ischemia, thrombotic stroke and global ischemia, secondary to cardiac arrest), other central nervous system disorders mediated by NO and other disorders mediated by NO.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering.

Compounds of the present invention are represented by the following chemical formula:

(I)

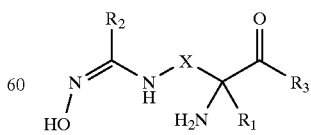

and pharmaceutically acceptable salts, wherein:

$R_1$ is not present or is selected from the group consisting of hydrogen, hydroxyalkyls, alkoxyalkyls, lower alkyls and haloalkyls;

$R_2$ is selected from the group consisting of straight and branched lower alkyls, lower alkenyls, and lower alkynyls, cycloalkyls, cycloalkenyls, and haloalkyls;

$R_3$ is selected from the group consisting of hydroxy, lower alkoxys, and natural and synthetic amino acids;

X is selected from the group consisting of lower alkylenes, lower alkenylenes and lower alkynylenes and which may optionally be substituted by one or more alkyl, alkoxy, hydroxy, halogen, trifluoromethyl, nitro, cyano, or amino groups; or X is selected from the group consisting of the formula —$(CH_2)_kQ(CH_2)_t$— where k is 1, 2 or 3, t is 1, 2 or 3 and Q is O, Se, $SiY_2$ where Y is lower alkyl, aryl, $S(O)_z$ where z is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —$(CH_2)_mA(CH_2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

It is an object of the present invention to provide compounds that have usefulness as inhibitors of nitric oxide synthase. These compounds also preferentially inhibit the inducible form over the constitutive form by at least 3 fold.

DETAILED DESCRIPTION OF THE INVENTION

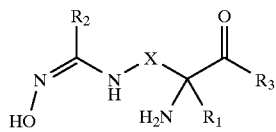

(I)

and pharmaceutically acceptable salts, wherein:

$R_1$ is not present or is selected from the group consisting of hydrogen, hydroxyalkyls, alkoxyalkyls, lower alkyls and haloalkyls;

$R_2$ is selected from the group consisting of straight and branched lower alkyls, lower alkenyls, and lower alkynyls, cycloalkyls, cycloalkenyls, and haloalkyls;

$R_3$ is selected from the group consisting of alkylaminos, hydroxy, lower alkoxys, and natural and synthetic amino acids;

X is selected from the group consisting of lower alkylenes, lower alkenylenes and lower alkynylenes and which may optionally be substituted by one or more alkyl, alkoxy, hydroxy, halogen, trifluoromethyl, nitro, cyano, or amino groups; or X is selected from the group consisting of the formula —$(CH_2)_kQ(CH_2)_t$— where k is 1, 2 or 3, t is 1, 2 or 3 and Q is O, Se, $SiY_2$ where Y is lower alkyl, aryl, $S(O)_z$ where z is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —$(CH_2)_mA(CH_2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

A preferred embodiment of the present invention is a compound of the formula (II):

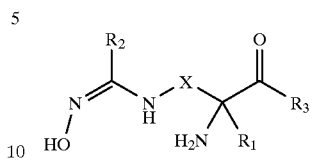

(II)

and pharmaceutically acceptable salts, wherein:

$R_1$ is not present or is selected from the group consisting of hydrogen, hydroxyalkyls, alkoxyalkyls, lower alkyls and haloalkyls;

$R_2$ is selected from the group consisting of straight and branched lower alkyls, lower alkenyls, and lower alkynyls, cycloalkyls, cycloalkenyls, and haloalkyls;

$R_3$ is selected from the group consisting of hydroxy, lower alkoxys, and natural and synthetic amino acids;

X is selected from the group consisting of alkylenes, alkenylenes and alkynylenes having 2 to 6 carbon atoms and which may optionally be substituted by one or more alkyl groups; or X is selected from the group consisting of the formula —$(CH_2)_kQ(CH_2)_t$— where k is 2 or 3, t is 1 or 2 and Q is O, Se, $SiY_2$ where Y is lower alkyl, aryl, $S(O)_Z$ where z is 0, 1 or 2, or NR where R is H or lower alkyl; or X is selected from the group consisting of the formula —$(CH_2)_mA(CH_2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

Another preferred embodiment of the present invention is a compound of the formula II and pharmaceutically acceptable salts; wherein:

$R_1$ is selected from the group consisting of hydrogen, hydroxyalkyls of 1 to 4 carbon atoms, lower alkyls of 1 to 8 carbon atoms and haloalkyls of 1 to 4 carbon atoms;

$R_2$ is selected from the group consisting of straight and branched lower alkyls of 1 to 4 carbon atoms, lower alkenyls and lower alkynyls of 2 to 4 carbon atoms, cycloalkyls of 3 to 6 carbon atoms, cycloalkenyls of 4 to 6 carbons, and haloalkyls of 1 to 4 carbon atoms;

$R_3$ is selected from the group consisting of hydroxy, lower alkoxys of 1 to 4 carbon atoms, and natural and synthetic amino acids;

X is selected from the group consisting of alkylenes, alkenylenes and alkynylenes having 2 to 6 carbon atoms and which may optionally be substituted by one or more alkyl groups; or X is selected from the group consisting of the formula —$(CH_2)_kQ(CH_2)_t$— where k is 2 or 3, t is 1 or 2 and Q is O (oxygen), Se, $SiY_2$ where Y is lower alkyl, aryl, $S(O)_z$ where z is 0, 1 or 2, or NR where R is H or lower alkyl; or X is selected from the group consisting of the formula —$(CH_2)_mA(CH2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

Another preferred embodiment of the present invention is a compound of the formula (II) and pharmaceutically acceptable salts; wherein:

$R_1$ is selected from the group consisting of hydrogen, hydroxyalkyls of 1 to 4 carbon atoms, and lower alkyls of 1 to 4 carbon atoms;

$R_2$ is selected from the group consisting of straight and branched lower alkyls of 1 to 4 carbon atoms, and haloalkyls of 1 to 4 carbon atoms;

$R_3$ is selected from the group consisting of hydroxy and lower alkoxys of 1 to 4 carbon atoms;

X is an alkylene having 3 to 5 carbon atoms and which may optionally be substituted by one or more $C_{1-3}$ alkyl groups; or X is selected from the group consisting of the formula —$(CH_2)_k Q(CH_2)_t$— where k is 2 or 3, t is 1 or 2 and Q is O, Se, $S(O)_z$ where z is 0, 1 or 2; or X is selected from the group consisting of the formula —$(CH_2)_m A(CH_2)_n$— where m is 0, 1 or 2, n is 0, 1 or 2, A is a 3 to 6 membered carbocyclic or heterocyclic ring, aromatic ring or heteroaromatic ring.

Another preferred embodiment of the present invention is a compound of the formula (II) and pharmaceutically acceptable salts; wherein:

$R_1$ is hydrogen;

$R_2$ is methyl;

$R_3$ is selected from the group consisting of hydroxy, and lower alkoxys of 1 to about 4 carbon atoms;

X is an alkylene having 3 to 5 carbon atoms.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic radical" means an unsaturated cyclic hydrocarbon radical with 3 to about 6 carbon atoms, wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazolinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazonyl, quinolinyl, and the like.

The term "aryl" means an aromatic hydrocarbon radical of 6 to about 14 carbon atoms, preferably 6 to about 10 carbon atoms. Examples of suitable aromatic hydrocarbon radicals include phenyl, naphthyl, and the like.

The terms "cycloalkyl" or "cycloalkenyl" means an "alicyclic radical in a ring with 3 to about 10 carbon atoms, and preferably from 3 to about 6 carbon atoms. Examples of suitable alicyclic radicals include cyclopropyl, cyclopropylenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The terms "lower alkylene", "lower alkenylenes" and "lower alkynylene" refers to hydrocarbons containing 2 to 10 carbon atoms, preferably 2 to 8 carbon atoms, and more preferably 2 to 6 carbon atoms.

The term "halogen" means fluorine, chlorine, bromine or iodine.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

The following general synthetic sequence is useful in making the present invention.

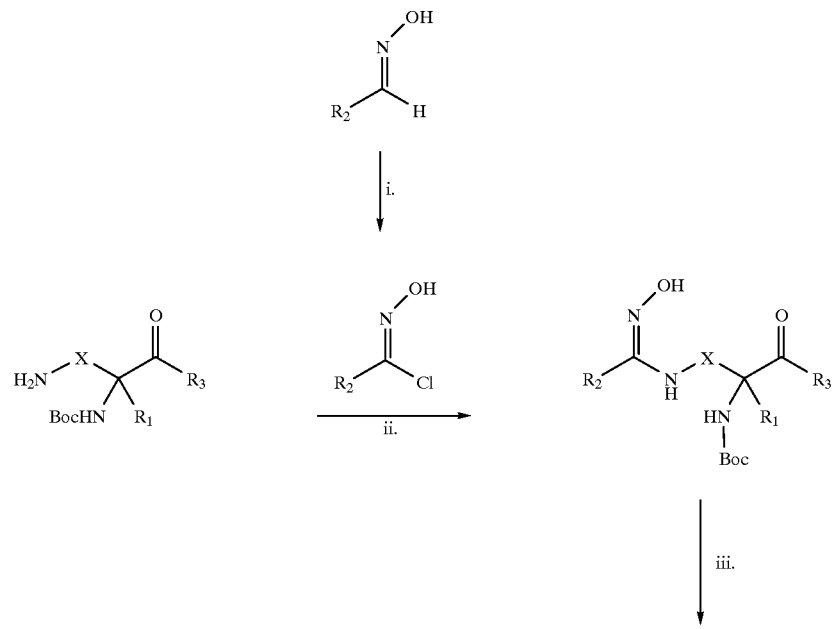

-continued

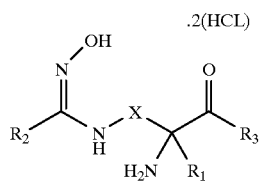

Legend:
i. N-Chlorosuccinimide, DMF
ii. H$_2$O pH = 9.5-10
iii. HCl

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous Na$_2$SO$_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from Varian VXR 300 MHz spectrometer with deuterium lock as an internal standard. $^{13}$C NMR spectra were obtained from a Varian spectrometer at 75 MHz with deuterium lock as an internal standard.

EXAMPLE 1

N$^6$-[1-(hydroxyimino)ethyl]-L-lysine, Dihydrochloride

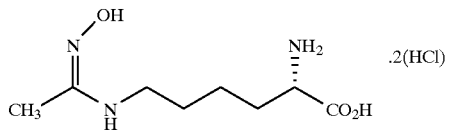

To a 125 mL flask was added 3 g (0.012 mol) of α-Boc-L-lysine and 70 mL of water. This solution was adjusted to pH=9.5 by addition of 2.5 N NaOH. To this solution was added portionwise, 2.3 g of chloroacetaldoxime which was prepared immediately prior to use by the reaction of 3.55 g (0.06 mol) of acetaldoxime with 10.4 g (0.78 mol) of N-chlorosuccinimide in 65 mL of N,N-dimethylformamide at 0° C. The chloroacetaldoxime was isolated after three hours by extracting into diethyl ether and washing with aqueous NaCl. Drying with MgSO$_4$, filtrating and concentrating under 30° C. afforded the chloroacetaldoxime as a pale yellow oil. During the chloroacetaldoxime addition, the pH was kept at 9.5 via concomitant addition of 2.5 N NaOH. After the addition was complete, the solution was allowed to stand at 25° C. for 25 minutes. The solution was then adjusted to pH=7.5 with 1N HCl and poured onto a Dowex 50 Cation exchange column. The column was washed with water. The Boc-protected product was then eluted with 10% aqueous pyridine. After concentrating, the product was deprotected by allowing it to stand in 2N HCl at 25° C. for two hours. Concentrating in vacuo afforded 2.9 g (78%) of L-N$^6$-(hydroximinoethyl)lysine dihydrochloride as a viscous yellow oil. $^1$H-NMR(D$_2$O)

1.25–1.45 (m, 2H), 1.5–1.6 (m, 2H), 1.75–1.9 (m, 2H), 2.05 (s, 3H), 3.25 (t, 2H), 3.95 (t, 1H); Mass Spectra, M+H=204.

EXAMPLE 2

N$^5$-[1-(hydroximino)ethyl]-2-methylornithine, Dihydrochloride

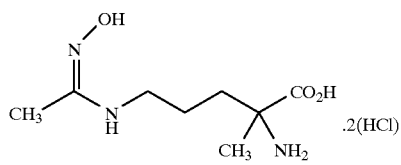

α-Methyl-D,L-ornithine hydrochloride is protected as a copper complex via reaction with cupric carbonate in refluxing water. This protected amino acid is then reacted with chloroacetaldoxime as in Example 1. The product is eluted from Dowex with 1N ammonium hydroxide. Concentration in vacuo, followed by acidification with hydrochloric acid affords the title compound.

EXAMPLE 3

N$^6$-[1-(hydroximino)ethyl]-2-methyllysine, Dihydrochloride

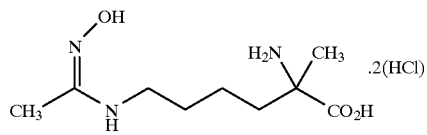

A suspension of lysine ethyl ester dihydrochloride (33 g; 0.14 mole) and MgSO$_4$ (34 g; 0.28 moles) in a solution of 4-chloro-benzaldehyde (39 g; 0.28 moles) and acetonitrile (500 mL) was stirred while N,N-diisopropylethylamine (36 g; 0.28 moles) was added in portions over ½ h. The mixture was stirred for 12 h, filtered, concentrated to a small volume, and diluted with 500 mL of diethyl ether. The ether solution was washed with 0.1% aqueous NaHCO$_3$, aqueous 2 N NaOH containing 2 g/100 ml of NH$_2$OH.HCl, again with 0.1% aqueous NaHCO$_3$ and saturated aqueous NaCl. After drying with MgSO$_4$ and removal of the solvent in vacuo, ethyl N, N'-di(4-chloro-phenylmethylene)-L-lysine was obtained as a clear liquid. The liquid was triturated with hexanes and the resulting solid was washed with hexanes several times. This partially purified intermediate was dissolved in 200 mL of THF and stirred in an acetone/dry ice bath. Sodium bis-(trimethylsilyl)amide in THF (11 mL, 1 M solution) was added dropwise over 30 min. After one hour, methyl iodide (0.8 g; 13 mmoles) in THF was added dropwise. The reaction mixture was slowly warmed up to room temperature and stirred overnight. The mixture was diluted with water, and extracted with ethyl ether. The ether extract was washed with 0.1% aqueous NaHCO$_3$ and saturated aqueous NaCl and concentrated to yield crude ethyl N.N'-di(4-chloro-phenylmethylene)-α-methyl-D,L-lysine (M+H=434). This material (4 g) dissolved in ethyl ether (100 ml) was stirred vigorously with 1 N HCl (50 mL) for 2 h, the layer was separated and the aqueous phase was washed with ethyl ether. The aqueous solution was further acidified by the addition of 6 N HCl and was heated to reflux for 16 h. The solution was cooled to room temperature, and rotary evaporated to dryness. The residue was dissolved in water and applied to a Dowex 50×4 (hydrogen form). The column was washed with water, and then 10% pyridine. α-Methyl-D,L-lysine, (M+H=161) was eluted from the column with 1 M NH$_4$OH. The α-methyl-D,L-lysine is protected as a copper complex via reaction with cupric carbonate in refluxing water. This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 4

3-[[2-[[1-(hydroxyimino)ethyl]amino]ethyl]selenyl]-2-methylalanine, Dihydrochloride

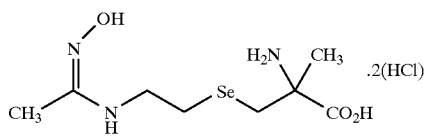

D,L-Selenocystine (117 mg; 0.5 mmoles, purchased from Sigma) was suspended in 15 mL of nitrogen (N$_2$) gas-purged water. Sodium borohydride (38 mg; 1 mole) was added. The reaction mixture became clear in a few minutes. After 2 h at room temperature, 2-bromoethylamine HCl (1.2 g; 6 mmoles) was added and the reaction mixture was stirred for 12 h. The reaction was applied on to a Dowex 50×4 (hydrogen form) column. The column was washed with water and 10% pyridine and 2-aminoethyl-selenocysteine was eluted with 1 M NH$_4$OH. The 2-aminoethyl-selenocysteine is protected and subsequently methylated as described in Example 3 to afford the α-methyl-(2-aminoethyl)selenocysteine. The α-methyl-(2-aminoethyl)selenocysteine is protected as a copper complex via reaction with cupric carbonate in refluxing water. This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 5

N$^6$-[1-(hydroximino)ethyl]-2-(hydroxymethyl) lysine, Dihydrochloride

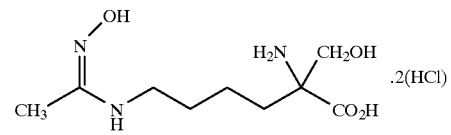

To an ice-cold stirred mixture of N$^ε$-Cbz-L-lysine (14 g; 0.05 moles, purchased from Sigma) in 2.5 N NaOH (24 mL), benzoyl chloride (10 g) was added gradually. The pH of the solution was maintained at 10.5–10.9 by addition of 2 N NaOH. The mixture was stirred at room temperature for 1 h and filtered. The filtrate was extracted with a small amount of ethyl acetate and the organic layer was dried over sodium sulfate. The solid was removed by filtration and the filtrate was evaporated to dryness. The crude oily N$^ε$-Cbz-N$^α$-benzoyl-lysine residue (6 g) was heated at 90–100° C. in acetic anhydride (100 mL) for 30 min. The mixture was then evaporated. The residue was dissolved in pyridine and treated with aqueous formaldehyde (35% solution, Fisher). The mixture was stirred for 8 hr and then diluted. The reaction mixture was kept at 10° C. overnight the precipitated crude material was hydrolyzed by boiling in 5 N HCl during 5 h. The reaction mixture was cooled and filtered before being evaporated. The solid residue was dissolved in water and passed through Dowex 50×4 (hydrogen form) column. α-Hydroxymethyl-D,L-lysine (MH$^+$=177) was eluted with 1 N NH$_4$OH. The α-hydroxymethyl-D,L-lysine is protected as a copper complex via reaction with cupric carbonate in refluxing water. This protected amino acid is then reacted with chloroacetaldoxime as described in Example 1. The product is eluted from Dowex with 1N ammonium hydroxide. Concentration in vacuo, followed by acidification with hydrochloric acid affords the title compound.

EXAMPLE 6

N$^6$-[2,2,2-trifluoro-1-(hydroxyimino)ethyl]-L-lysine, Dihydrochloride

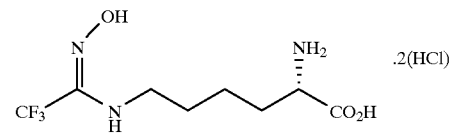

α-Boc-L-lysine is reacted with chlorotrifluoroacetaldoxime (J. Org. Chem. 49, (1984) 919–922) as described in Example 1 to afford the title compound.

Biological Data

The subject compounds of formula (I) have been found to inhibit nitric oxide synthase and posses useful pharmacological properties as demonstrated in one or more of the following assays:

Citrulline Assay for Nitric Oxide Synthase

NOS activity was measured by monitoring the conversion of L-[2,3-$^3$H]-arginine to L-[2,3-$^3$H]-citrulline. Mouse inducible NOS (miNOS) was prepared from an extract of LPS-treated mouse RAW 264.7 cells and rat brain constitutive NOS (rnNOS) was prepared from an extract of rat cerebellum. Both preparations were partially purified by DEAE-Sepharose chromatography. Enzyme (10&L) was added to 40 &L of 50 mM Tris (pH 7.6) and the reaction initiated by the addition of 50 &L of a solution containing 50 mM Tris (pH 7.6), 2.0 mg/mL bovine serum albumin, 2.0 mM DTT, 4.0 mM CaCl$_2$, 20 &M FAD, 100 &M tetrahydrobiopterin, 2.0 mM NADPH and 60 &M L-arginine containing 0.9 &Ci of L-[2,3-$^3$H]-arginine. For constitutive NOS, calmodulin was included at a final concentration of 40 nM. Following incubation at 37° C. for 15 minutes, the reaction was terminated by addition of 300 &L cold buffer containing 10 mM EGTA, 100 mM HEPES (pH5.5) and 1.0 mM L-citrulline. The [$^3$H]-citrulline was separated by chromatography on Dowex 50W X-8 cation exchange resin and radioactivity quantified with a liquid scintillation counter.

Raw Cell Nitrite Assay

RAW 264.7 cells are plated to confluency on a 96-well tissue culture plate grown overnight (17h) in the presence of LPS to induce NOS. A row of 3–6 wells were left untreated and served as controls for subtraction of nonspecific background. The media was removed from each well and the cells are washed twice with Kreb-Ringers-Hepes (25 mM, pH 7.4) with 2 mg/ml glucose. The cells are then placed on ice and incubated with 50 mL of buffer containing L-arginine (30 mM) +/- inhibitors for 1h. The assay is initiated by warming the plate to 37° C. in a water bath for 1h. Production of nitrite by intracellular iNOS is linear with time. To terminate the cellular assay, the plate of cells is placed on ice and the nitrite-containing buffer removed and analyzed for nitrite using a previously published fluorescent determination for nitrite. T. P. Misko et al, *Analytical Biochemistry*, 214, 11–16 (1993). All values are the average of triplicate wells and are compared to a background-subtracted induced set of cells (100% value).

In Vivo Assay

Rats were treated with an intraperitoneal injection of 10 mg/kg of endotoxin (LPS) with or without oral administration of the nitric oxide synthase inhibitors. Plasma nitrites were measured 5 hours post-treatment. The results show that the administration of the nitric oxide synthase inhibitor decreases the rise in plasma nitrites, a reliable indicator of the production of nitric oxide, induced by endotoxin.

TABLE I

Rodent (Cell Data and in vitro Enzyme Data)

| Compound | miNOS* IC50 [μM] | rnNOS* | Raw Cell* IC50 [μM] |
|---|---|---|---|
| Example 1 | 77 | 1470 | 28 |

*miNOS refers to mouse inducible NOS
rnNOS refers to rat brain constitutive NOS
Raw Cell refers to cultured RAW 264.7 cells

TABLE II

Human (in vitro Enzyme Data)

| Compound | hiNOS* | hecNOS* | hncNOS* IC50 [μM] |
|---|---|---|---|
| Example 1 | 154 | 1474 | 907 |

*hiNOS refers to recombinant human inducible NOS
hecNOS refers to recombinant human endothelial constitutive NOS
hncNOS refers to recombinant human neuronal constitutive NOS

TABLE III

Low Dose LPS*

| | in vivo Effective Dose (p.o., mg/kg/day) | | |
|---|---|---|---|
| Compound | 0.1 | 1 | 10 |
| Example 1 | 0% inh. | 54% inh. | 97% inh. |

*Low Dose LPS refers to the in vivo low-endotoxin assay carried out on rats as described above.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound having the formula;

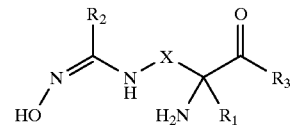

and pharmaceutically acceptable salts, wherein:

$R_1$ is not present or is selected from the group consisting of hydrogen, hydroxyalkyls, alkoxyalkyls, lower alkyls and haloalkyls;

$R_2$ is selected from the group consisting of straight and branched lower alkyls, lower alkenyls, and lower alkynyls, cycloalkyls, cycloalkenyls, and haloalkyls;

$R_3$ is selected from the group consisting of hydroxy, lower alkoxys, and natural and synthetic amino acids;

X is selected from the group consisting of lower alkylenes, lower alkenylenes and lower and which may optionally be substituted by one or more alkyl, alkoxy, hydroxy, halogen, trifluoromethyl, nitro, cyano, or amino groups; or X is selected from the group consisting of the formula —(CH$_2$)$_k$Q(CH$_2$)$_t$— where k is 1, 2 or 3, t is 1, 2 or 3 and Q is O, Se, SiY$_2$ where Y is lower alkyl, aryl, S(O)$_z$ where z is 0, 1 or 2, or NR where R is H or lower alkyl which may be optionally substituted with lower alkyl, lower alkoxy, hydroxy, halogen, trifluoromethyl, nitro, cyano, amino; or X is selected from the group consisting of the formula —(CH$_2$)$_m$A(CH$_2$)$_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

2. A compound having the formula;

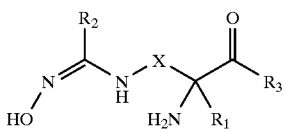

and pharmaceutically acceptable salts, wherein:
$R_1$ is not present or is selected from the group consisting of hydrogen, hydroxyalkyls, alkoxyalkyls, lower alkyls and haloalkyls;
$R_2$ is selected from the group consisting of straight and branched lower alkyls, lower alkenyls, and lower alkynyls, cycloalkyls, cycloalkenyls, and haloalkyls;
$R_3$ is selected from the group consisting of hydroxy, lower alkoxys, and natural and synthetic amino acids;
X is selected from the group consisting of alkylenes, alkenylenes and alkynylenes having 2 to 6 carbon atoms and which may optionally be substituted by one or more alkyl groups; or
x is selected from the group consisting of the formula —$(CH_2)_kQ(CH_2)_t$— where k is 2 or 3, t is 1 or 2 and Q is O, Se, $SiY_2$ where Y is lower alkyl, aryl, $S(O)_z$ where z is 0, 1 or 2, or NR where R is H or lower alkyl; or
X is selected from the group consisting of the formula —$(CH_2)m_A(CH_2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

3. The compound as recited in claim 2 wherein
$R_1$ is selected from the group consisting of hydrogen, hydroxyalkyls of 1 to 4 carbon atoms, lower alkyls of 1 to 8 carbon atoms and haloalkyls of 1 to 4 carbon atoms;
$R_2$ is selected from the group consisting of straight and branched lower alkyls of 1 to 4 carbon atoms, lower alkenyls and lower alkynyls of 2 to 4 carbon atoms, cycloalkyls of 3 to 6 carbon atoms, cycloalkenyls of 4 to 6 carbons, and haloalkyls of 1 to 4 carbon atoms;
$R_3$ is selected from the group consisting of hydroxy, lower alkoxys of 1 to 4 carbon atoms, and natural and synthetic amino acids;
X is selected from the group consisting of alkylenes, alkenylenes and alkynylenes having 2 to 6 carbon atoms and which may optionally be substituted by one or more alkyl groups; or
X is selected from the group consisting of the formula —$(CH_2)_kQ(CH_2)_t$— where k is 2 or 3, t is 1 or 2 and Q is O (oxygen), Se, $SiY_2$ where Y is lower alkyl, aryl, $S(O)_z$ where z is 0, 1 or 2, or NR where R is H or lower alkyl; or
X is selected from the group consisting of the formula —$(CH_2)_mA(CH_2)_n$— where m is 0, 1 or 2, n is 0, 1 or 2, A is a 3 to 6 membered carbocyclic or heterocyclic ring, aromatic ring or heteroaromatic ring which may optionally be substituted by one or more substituents selected from the group consisting of lower alkyl, lower alkoxy, hydroxy, halogen, nitro, cyano, trifluoroalkyl and amino.

4. The compound as recited in claim 3 wherein
$R_1$ is selected from the group consisting of hydrogen, hydroxyalkyls of 1 to 4 carbon atoms, and lower alkyls of 1 to 4 carbon atoms;
$R_2$ is selected from the group consisting of straight and branched lower alkyls of 1 to 4 carbon atoms, and haloalkyls of 1 to 4 carbon atoms;
$R_3$ is selected from the group consisting of hydroxy, and lower alkoxys of 1 to 4 carbon atoms;
X is an alkylene having 3 to 5 carbon atoms and which may optionally be substituted by one or more $C_{1-3}$ alkyl groups; or
X is selected from the group consisting of the formula —$(CH_2)_kQ(CH_2)_t$— where k is 2 or 3, t is 1 or 2 and Q is O, Se, $S(O)_z$ where z is 0, 1 or 2; or
X is selected from the group consisting of the formula —$(CH_2)_mA(CH_2)_n$— where m is 0, 1 or 2, n is 0, 1 or 2, A is a 3 to 6 membered carbocyclic or heterocyclic ring, aromatic ring or heteroaromatic ring.

5. The compound as recited in claim 4 wherein
$R_1$ is hydrogen;
$R_2$ is methyl;
$R_3$ is selected from the group consisting of hydroxy, and lower alkoxys of 1 to about 4 carbon atoms;
X is an alkylene having 3 to 5 carbon atoms.

6. A compound as recited in claim 5 wherein said compound is selected from the group consisting of;
$N^6$-[1-(hydroxyimino)ethyl]-L-lysine, dihydrochloride;
$N^5$-[1-(hydroximino)ethyl]-2-methylornithine, dihydrochloride;
$N^6$-[1-(hydroximino)ethyl]-2-methyllysine, dihydrochloride;
3-[[2-[[1-(hydroxyimino)ethyl]amino]ethyl]selenyl]-2-methylalanine, dihydrochloride;
$N^6$-[1-(hydroximino)ethyl]-2-(hydroxymethyl)lysine, dihydrochloride; and
$N^6$-[2,2,2-trifluoro-1-(hydroxyimino)ethyl]-L-lysine, dihydrochloride.

7. A method of inhibiting nitric oxide synthesis in a subject in need of such inhibition by administering a therapeutically effective amount of a compound of claims 1, 2, 3, 4, 5, or 6.

8. A method of selectively inhibiting nitric oxide synthesis produced by inducible NO synthase over nitric oxide produced by the constitutive forms of NO synthase in a subject in need of such selective inhibition by administering a therapeutically effective amount of a compound of claims 1, 2, 3, 4, 5, or 6.

9. A method of lowering nitric oxide levels in a subject in need of such by administering a therapeutically effective amount of a compound of claims 1, 2, 3, 4, 5, or 6.

10. A pharmaceutical composition comprising a compound of claims 1, 2, 3, 4, 5, or 6 together with one or more pharmaceutically acceptable carriers.

* * * * *